United States Patent
Sinfield et al.

(10) Patent No.: US 9,488,582 B2
(45) Date of Patent: Nov. 8, 2016

(54) METHODS FOR MEASURING CONCENTRATIONS OF CHLORINATED SOLVENTS THROUGH RAMAN SPECTROSCOPIC OBSERVATION OF THE VIBRATIONAL MODES OF WATER

(71) Applicant: Purdue Research Foundation, West Lafayette, IN (US)

(72) Inventors: Joseph Victor Sinfield, West Lafayette, IN (US); Chukwukelue Kenneth Monwuba, Baltimore, MD (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 14/656,136

(22) Filed: Mar. 12, 2015

(65) Prior Publication Data

US 2015/0260655 A1 Sep. 17, 2015

Related U.S. Application Data

(60) Provisional application No. 61/953,335, filed on Mar. 14, 2014.

(51) Int. Cl.
*G01N 21/65* (2006.01)
*G01N 33/18* (2006.01)

(52) U.S. Cl.
CPC ............ *G01N 21/65* (2013.01); *G01N 33/182* (2013.01); *Y10T 436/193333* (2015.01)

(58) Field of Classification Search
CPC ........................... G01N 21/65; G01N 33/182
See application file for complete search history.

(56) References Cited

PUBLICATIONS

Acha, V. et al., "Detoxification of a mixture of 663 aliphatic chlorinated hydrocarbons in a fixed-bed bioreactor: continuous on-line monitoring via an attenuated total reflection-Fourier transform infrared sensor." Water Science and 665 Technology,40(8), 41-4, 1999.
Bhattacharyya, J., et al., "Biosensor-based diagnostics of contaminated groundwater: Assessment and remediation 668 strategy." Environmental Pollution 34(3): 485-492, 2005.
Bilodeau, T. G., et al., "Fiber optic Raman probe detection of chlorinated hydrocarbons in standard soils." Proceedings of SPIE—The International Society for Optical Engineering, 2068, 258-270, 1994.
Bloch, J., et al., "Field test of a novel microlaser-based probe for in-situ fluorescence sensing of soil contaminants." Applied Spectroscopy, 52(10), 1299-1304, 1998.
Bradley, E. B., et al., "On the exploitation of laser Raman spectroscopy for detection and identification of molecular water pollutants." Water Research, v4, 125-128, 1970.
Burck, J., et al., "Fiber optic NIR evanescent wave absorption sensor systems for in situ monitoring of hydrocarbon compounds in waste and ground water." Proceedings of SPIE—The International Society for Optical Engineering, 3534, 222-233, 1999.
Burgess, S., et al., "Fluorescence suppression in time-resolved Raman spectra." Journal of Physics E: Scientific Instruments, 10, 617-620, 1977.
Busing, W. R., et al., The Effect of Dissolved KBr, KOH or HCl on the Rman Spectrum of Water. Journal of Physical Chemistry 65 (2) 284-29, 1960.
Carey, D. M., et al., "Measurement of the Rman spectrum of liquid water." Journal of Chemical Physics, v 108 (7) 2669-2675, 1998.
Coker, D. F., et al., "Structure and Vibrational spectroscopy of the water dimer using quantum simulation." Journal of Physical Chemistry, v 91, (10) 2513-18, 1987.
Daley, P. F., et al., "Fiber optic sensor for continuous monitoring of chlorinated solvents in the vadose zone and in groundwater: field test results." Proceedings of SPIE—The International Society for Optical Engineering, 1587, 278-282, 1992.
Degrandpre, M. D., et al., "A fiber-optic FT-NIR evanescent field absorbance sensor." Applied Spectroscopy, 44(2), 273-279, 1990.
Fraser, R. et al., Resolution of overlapping bands: Functions for simulating band shapes. Analytical Chemistry 41(1), 37-39, 1969.
Ge, Y. et al., "Remote sensing of soil properties in precision agriculture: a review." Paper No. 061176, Annual International Meeting of the American Society of Agricultural and Biological Engineers, Jul. 9-12, 2006. Portland, OR.
Gobel, R. et al., "Infrared attenuated total reflection spectroscopic investigations of the diffusion behaviour of chlorinated 714 hydrocarbons into polymer membranes." Vibrational Spectroscopy, 8(2), 141-149, 1995.
Grimm, R., et al., "Nonlinear complex-resistivity survey for DNAPL at the savannah river site A-014 outfall." Journal of Environmental and Engineering Geophysics, 10(4), 351-364, 2005.
Holt, B. D., et al., "Extraction of chlorinated aliphatic hydrocarbons from groundwater at micromolar concentrations for isotopic analysis of chlorine." Environmental Pollution, 113(3), 263-269, 2001.
Howley, R., et al., "A study of the factors affecting the diffusion of chlorinated hydrocarbons into polyisobutylene and polyethylene-co-propylene for evanescent wave sensing." Vibrational Spectroscopy, 31(2) 271-278, 2001.
Idriss, A. (2001). "Study of aqueous acetone solution at various concentrations:low frequency Raman and molecular dynamics simulations." Journal of Physical Chemistry B, 105 (250 729 6004-9.

(Continued)

*Primary Examiner* — Paul Hyun
(74) *Attorney, Agent, or Firm* — Purdue Research Foundation

(57) ABSTRACT

Method for determining concentration of a chlorinated solvent in a non-turbid aqueous solution sample containing the chlorinated solvent is disclosed. The method includes developing a calibration profile relating intensities of Raman returns at a predetermined Raman shift associated with O—H stretching region of water for non-turbid aqueous chlorinated solvent calibration solutions of known concentrations. Intensity of Raman return at the predetermined Raman shift associated with O—H stretching region of the non-turbid aqueous solution sample is measured and compared to the calibration profile to determine the concentration of the chlorinated solvent in the non-turbid aqueous solution sample. For turbid solution samples, a method using turbidity-corrected intensity for the solution sample is disclosed. Alternatively, for turbid solution samples, a method employing a calibration profile utilizing turbid calibration solutions is disclosed.

20 Claims, 7 Drawing Sheets

(56) References Cited

PUBLICATIONS

Jakusch, M., et al., "Towards a remote IR fiber-optic sensor system for the determination of chlorinated hydrocarbons in water." Sensors and Actuators B: Chemical, 38(1-3), 83-87, 1997.
Conzen, J., et al., "Characterizaiton of a fiber-optic evanscent wave absorbance sensor for Nonpolar organic compounds." Applied Spcectroscopy, vol. 47, No. 6, 753-763, 1993.
Jorgensen, W. L. et al., "Ab Initio Study of Structures and Binding Energies for Anion-Water Complexes." Journal of American Chemical Society, 108, 478-479, 1987.
Kato, M., et al., "Use of SCAPS petroleum hydrocarbon sensor technology for real-time indirect DNAPL detection." Journal of Soil Contamination, 7 (1), 73-86, 1998.
Kram, M. L., et al. "DNAPL characterization methods and approaches, Part 1: Performance comparisons." Ground Water Monitoring and Remediation, 21(4), 109-123, 2001.
Langford, J. I., "A Rapid Method for Analyzing the Breadths of Diffraction and Spectral Lines using the Voigt function." Journal of Applied Crystallolgy. 11, 10-14, 1978.
Li, R., et al., "Hydrogen bonded structure of water and aqueous solutions of sodium halides: a Raman spectroscopic study." Journal of Molecular Structure 707, 83-88, 2004.
Lin, J., et al., "Subsurface contaminant monitoring by laser fluorescence excitation-emission spectroscopy in a cone penetrometer probe." Proceedings of SPIE—The International Society for Optical Engineering, 2504, 59-67, 1995.
Malandain, C., et al., "Biosensors for the environment." Oil and Gas Science and Technology, 60 (6), 887-897, 2005.
Miano, T., et al., Flourescence Spectroscopy of Humic Substances. Soil Sci. Soc. Am. J., 52(4), 1016-1019, 1988.
Marcus, Y. "Effect of Ions on the Structure of Water: Structure making and Breaking." Chemical Reviews, 109, 1346-1370, 2009.
Mehran, M, et al., "Distribution Coefficient of Trichloroethylene in Soil-Water Systems." Ground Water 25(3): 275-282, 1987.
Morris, M., D., et al., "Detection of Chlorinated Hydrocarbons in Aqueous Surfactant Solutions by Near-IR Raman Spectroscopy" Applied Spectroscopy, v49 (8) 1146-1150, 1995.
Mullen, K., et al., "Adsorption of Chlorinated Ethylenes at 1-Octadecanethiol-Modified Silver Surfaces." Analytical Chemistry 66(4): 478-483, 1994.
Pack, B. W., et al., "Determination of halogenated hydrocarbons by helium microwave plasma torch time-of-flight mass spectrometry coupled to gas chromatography." Analytical Chemistry, 70(18), 3957-3963, 1998.
Rossabi, J., et al., "Field tests of a DNAPL characterization system using cone penetrometer-based Raman spectroscopy." Ground Water Monitoring and Remediation, 20(4), 72-81, 2000.
Sinfield, J. V., et al., "A Low Cost Time-Resolved Spectrsocopic Sensing System Enabling Fluorescence Rejection," Applied Spectroscopy. 64 (2) 201-210, 2010.
Smith, J., D., et al., "The Effects of Dissolved Halide Anions on Hydrogen Bonding in Liquid Water." Journal of the American Chemical Society, 129, 13847-13856, 2007.
Soderholm, S., et al., "Raman Spectra of Fructose and Glucose in the Amorphous and Crystalline States." Journal of Raman Spectroscopy, 30, 1009-1018, 1999.
Stone, H., "Mathematical Resolution of Overlapping Spectral Lines." Journal of Optical Society of America. 52, 998-1000, 1962.
Storey, J., et al., "Electrochemical SERS Detection of Chlorinated Hydrocarbons in Aqueous Solutions", Applied Spectroscopy, 48, 10, pp. 1265-1271, 1994.
Syage, J. A., et al., "Field-portable, high-speed GC/TOFMS." Journal of the American Society for Mass Spectrometry, 12(6), 648-655, 2001.
Terpstra, P., et al., "Effect of salts on dynamics of water: A Raman spectroscopy study." Journal of Chemical Physics 92 (1) 65-70, 1990.
Van Vacker, et al., "GC/multiple collector-ICPMS method for chlorine stable isotope analysis of chlorinated aliphatic hydrocarbons." Analytical Chemistry, 78(13), 4663-4667, 2006.
Wahl, J. H., et al., "A portable multi-dimensional gas chromatographic system for field applications." Journal of Separation Science, 26(12-13), 1083-1090, 2003.
Monwuba, C. K., et al., The Effect of Turbidity on Raman Spectroscopic Analysis of Aqueous Chlorinated Samples. GeoCongress 2012 © ASCE 2012, 3408-3418.
Kruse, J., et al., "Remote sensing of nitrogen stress in creeping bentgrass." Agronomy Journal, 98, 1640-1645, 2006.

METHODS FOR MEASURING CONCENTRATIONS OF CHLORINATED SOLVENTS THROUGH RAMAN SPECTROSCOPIC OBSERVATION OF THE VIBRATIONAL MODES OF WATER

CROSS-REFERENCE TO RELATED APPLICATIONS

The present U.S. patent application is related to and claims the priority benefit of U.S. Provisional Patent Application Ser. No. 61/953,335, filed Mar. 14, 2014, the contents of which hereby incorporated by reference in their entirety into the present disclosure.

STATEMENT REGARDING GOVERNMENT FUNDING

This invention was made with government support under CMMI0927112 awarded by the National Science Foundation. The government has certain rights in the invention.

TECHNICAL FIELD

The present disclosure generally relates to methods and apparatus for determining concentrations of chlorinated solvents in aqueous solutions of chlorinated solvents through Raman spectroscopy, and in particular by Raman spectroscopic observation of vibrational modes of water.

BACKGROUND

This section introduces aspects that may help facilitate a better understanding of the disclosure. Accordingly, these statements are to be read in this light and are not to be understood as admissions about what is or is not prior art.

Improvements in diode laser, fiber optic, and data acquisition technologies are enabling increased use of Raman spectroscopic techniques for both in-lab and in-situ water analysis. In this disclosure "in-situ" is used to describe a situation in which the measurement or action is or can be performed directly at the source of a sample in the field. Thus in this disclosure "in-situ" can be used interchangeably with each of "in the field", "on-site, "in-line" and "in-flow".

Production and environmental release of chlorinated aliphatic hydrocarbons peaked between the late eighties and early nineties. Due to their widespread use in the production of household products, degreasing operations, and petroleum refining, chlorinated solvents have become ubiquitous pollutants. According to the Environmental Protection Agency's (EPA) Toxic Chemical Release Inventory, between 1987 and 1993, releases to water and land of trichloroethylene (TCE), 1,2-Dichloroethane (1,2-DCA), Dichloromethane (DCM), and 1,1,1-33 Trichloroethane (1,1,1-TCA) totaled over 1.7 million kg, representing only a subset of all chlorinated solvents thus released. These contaminants are still known to persist in the environment and it has been reported that up to 34% of the drinking water supply sources in the U.S. likely contain TCE contamination. Compounds such as trichloroethylene (TCE) and tetrachloroethene (PCE) are found at approximately 80% of all Superfund sites with groundwater contamination (852 facilities) and more than 3000 Department of Defense (DoD) sites in the U.S. The net result is that these solvents pose a considerable threat as groundwater contaminants and account for a significant proportion of the more than 90 contaminants of drinking water listed by the EPA.

Chlorinated solvents are Dense Non-Aqueous Phase Liquids (DNAPLs) and are denser than water and thus when spilled or released into the environment tend to migrate downward in the subsurface. Their migration through the vadose zone can lead to residual pockets of contaminants in soil pore spaces (source zones), the release of vapors in soil pore space, dissolution in groundwater (to the extent possible) in the capillary fringe and below the groundwater table, and pooling above an aquitard, as well as continued infiltration into fractures in boundary rock layers. The tendency for these compounds to partition (i.e. capable of going into solution) makes them exceptionally menacing pollutants. While the fate and transport of the dissolved fractions are influenced by phenomenon such as groundwater advection, mechanical dispersion, molecular diffusion, and groundwater-porous media chemical partitioning, movement of the compounds can be significantly influenced by gravity and capillary effects that make it difficult to adequately characterize and track their presence in the subsurface. The sporadic and localized concentration of chlorinated solvents in regions such as soil pores and retarded pools also serves as a recalcitrant contaminant source which can often frustrate remediation attempts.

The unique challenges posed by chlorinated solvent DNAPLs in the geoenvironment have led both the U.S. EPA and the National Academy of Sciences to conclude that DNAPL sources may be contained, but remediation to typical cleanup levels for most DNAPL sites is often "technically impracticable" at justifiable costs This realization has driven a shift in the strategies pursued to deal with sites contaminated with chlorinated solvents. Most notably, added attention has been given to the potential to pursue "monitored natural attenuation" (MNA) rather than or in combination with proactive remediation. This site management approach relies upon natural physical, chemical and biological processes to reduce contaminant concentrations. In this context, application of mass balance principles must demonstrate that the summation of the effects of available natural attenuation mechanisms will be sufficient to remediate the site and protect vulnerable interests. Successful application of MNA typically requires extensive site analyses for initial screening for MNA potential, verification of attenuation processes, confirmation of effective MNA, and long term monitoring for any changes to the natural system that could alter the potential to achieve remediation goals. While initially conceived as a cost effective alternative to proactive remedial intervention it is becoming clear that the costs of site characterization and long term monitoring may be prohibitive, and so significant effort has been focused on developing more cost-effective approaches to carry out these tasks.

Currently, the technology used in common practice to assess chlorinated solvent levels in a contaminated site with actionable reliability involves either very costly and/or sophisticated laboratory instrumentation or expensive field instruments that can assess only a limited set of compounds, provide information over a limited spatial extent, and/or are too costly or complex to lend themselves to continuous long-term monitoring scenarios. Attempts to measure the effects of remediation efforts or the availability of attenuation mechanisms, for example to support mass balance evaluations of monitored natural attenuation, are even more challenging. The challenges are due to associated complexities such as inaccessibility of ground environment and simultaneous action of multiple attenuation mechanisms.

In the realm of laboratory measurements of chlorinated solvents and their daughter compounds, a host of wet chemistry techniques are applied. Chief among these techniques are: variants of gas chromatography-mass spectrometry (GC-MS) that have been adapted to perform stable isotope analysis of carbon and chlorine to assess levels of chlorinated aliphatic hydrocarbons while mitigating alteration of sample components resulting from pre-processing (e.g., Helium Microwave Induced Plasma MS to GC); and, carrier gas extraction to GC multiple collector inductively coupled plasma-source mass spectrometry (MC-ICPMS). While these techniques require field acquisition of samples (e.g., with devices such as the Waterloo profiler or precision injection/extraction probes and subsequent laboratory preparation and analysis which is are time consuming and expensive processes, they yield highly chemical-specific results with great sensitivity (ppb or better).

In the field, remote sensing techniques (primarily satellite based) provide general information on field conditions or inferential indications of contaminant presence (such as foliage discoloration or depletion), yet offer limited resolution (typically several square meters), and provide virtually no insight into subsurface conditions. Geophysical methods, such as electrical resistivity imaging and non-linear complex-resistivity cross-hole imaging, can successfully indicate the presence of chlorinated solvents in-situ, but typically at limited depths, spatial resolution, and sensitivity. Concepts that involve the introduction of foreign materials, such as graphite, Zeolite, or Samms particles, into the subsurface to enhance geophysical signatures have been proposed. Portable GC/MS units have also emerged commercially, but again require considerable sample handling. Other novel field approaches to chlorinated solvent evaluation include single point sensors that use replenishable reagents or biosensors but any one sensor of this type tends to have limited versatility. Beyond these techniques, an array of indirect methods are employed to indicate the presence of DNAPLs such as chlorinated solvents including use of reactive inter-well tracers, radon flux sensors, soil vapor probes, and membrane interface probes that monitor related volatiles However, these in-situ techniques tend to provide only directional input on the presence of contaminants or provide information over a very limited spatial extent.

In other cases, sensors are incorporated into cone penetrometer-type devices, and used to make direct field measurements. These instruments provide flexibility by enabling the investigator to rapidly examine multiple points in the field, both spatially and at depth, while limiting the errors that can often accompany sample extraction techniques, and thus their use has become increasingly common in practice. The majority of these direct penetrometer-based systems make use of optical spectroscopic phenomenon. Near-infrared (NIR) probes have been explored, as well as optical fiber sensors that rely on evanescent field phenomenon. However, these devices by their very nature apply only to compounds which absorb at the frequency of the system excitation source. Ultra-violet (UV) Laser Induced Fluorescence has also been explored, but tends to have difficulty yielding chemical specific or quantitative insights due to the overlap of fluorescence signatures of similar compounds. Some of the most promising results in this arena stem from work done with continuous wave (CW) Raman spectroscopy which has been shown to yield highly specific chemical signatures even in complex in-situ settings. Effectiveness of Raman systems, however, has traditionally been adversely affected by fluorescence interference in natural environments. More recently demonstrated is the ability to significantly suppress the impact of fluorescence on Raman observations by employing pulsed-laser technology to perform Time Resolved Raman Spectroscopy and effectively gate Raman from fluorescence phenomenon in the time-domain, with a closed-path fiber optic system that could be incorporated in a penetrometer or in a field monitoring station.

Despite these advances, in-situ analyses, which are necessary for cost effective site management, inevitably involve tradeoffs between the time and cost associated with the analysis, and the degree to which the results represent actual field conditions and can provide information of actionable quality. In particular, one of the biggest challenges with arguably the most versatile of the optical techniques, Raman spectroscopy, is its overall sensitivity In some studies, direct Raman analysis was performed on samples of Ottawa sand and two NIST (National Institute of Standards and Testing) soils, saturated with neat TCE, using the 488 nm line of a 100 mW Argon laser. In these studies the researchers reported clear evidence of the C—Cl vibrational mode at 628 cm-1, but the intensity of the Raman line did not correlate well to the soil mass fraction of the compound, indicating presence but providing little ability to quantify in-situ concentrations. In 1999, the USDOE (US Department of Energy) reported on the second generation of a cone-penetrometer equipped with a 785 nm CW Raman system (originally a 415 nm system) which was employed in two distinct in-situ settings to a) evaluate DNAPL contaminated radioactive waste in large containment vessels and b) assess DNAPL contamination directly in soils. For the in-tank tests, "the Raman probe demonstration resulted in more than 99 percent accuracy for compound identification and greater than 93 percent accuracy in identifying both the compounds and the concentration" for organic constituents above 20% by weight. For the direct push soil tests, the Raman probe was reported to be effective at detecting PCE at the "highest levels of contamination" in saturated zones (~1,500 ppm by mass), and was less reliable in the vadose zone. Later work made use of a 300 mW 785 nm CW laser and successfully detected the presence of TCE in-situ in proximity to a solvent storage tank at locations with depth that were later verified in the laboratory to contain concentrations of 200-750 ppm by mass TCE, but failed to detect TCE in other zones with concentrations on the order of 50 ppm by mass. No major advances in in-situ Raman analysis of chlorinated solvents have been reported for the last decade.

These initial studies helped define the value of even coarse in-situ Raman analysis and several commercially available cone-penetrometer Raman probe systems now exist. However, to date, these probes are generally used for rapid detect-non-detect profiling as detection limits have been high relative to chlorinated solvent concentrations typically present in the field. This is due to an inability to manage interference in the field and separate that interference from desired observations and the fact that the systems have traditionally used low resolution CCD detectors, an issue that limits a system's ability to differentiate two varying analyte concentrations.

Sites contaminated with chlorinated solvents frequently contain the pollutant at levels ranging from a neat state to low ppb concentrations that exceed Maximum Contaminant Level (MCL) drinking water standards (e.g., TCE MCL=5 ppb), with aqueous concentrations of 3 to 500 ppm commonly encountered in groundwater. By comparison, the detection levels reported in the historical studies noted above, which are on a mass of soil basis, are equivalent to ~300 to 9000 ppm on a volume to volume basis in the pore fluid of a soil (assuming a typical range of soil void ratios from 0.3 to 1.2 for the soils studied). To this end, any improvements to the sensitivity and resolution of a monitoring technology can be very valuable to facilitate enhanced plume delineation, earlier warnings of contaminant release from a containment zone, and/or the design of more tailored monitoring approaches.

Due to the factors mentioned above, a need exists for a method and apparatus to improve the overall sensitivity of Raman observations of chlorinated solvents through indirect measurements that take advantage of the influence of chlorine on the vibrational modes of water to indicate the presence of chlorinated compounds in solution.

SUMMARY

A method for determining concentration of a chlorinated solvent in a non-turbid aqueous solution sample containing the chlorinated solvent is disclosed. The method includes providing a set of non-turbid aqueous chlorinated solvent calibration solutions. Each of the non-turbid calibration solutions includes solutions of water and a chlorinated solvent and each non-turbid calibration solution has a concentration of the chlorinated solvent within a predetermined concentration range. Further, at least two of the chlorinated solvent calibration solutions in the set have different concentrations of the chlorinated solvent within the predetermined concentration range. The intensity of Raman return at a predetermined Raman shift associated with O—H stretching region of water for each of the non-turbid aqueous chlorinated solvent calibration solutions is measured. A calibration profile for non-turbid solutions is then developed relating chlorinated solvent concentrations of the non-turbid aqueous chlorinated solvent calibration solutions in the set to these measured intensities. The non-turbid aqueous solution sample, which contains the chlorinated solvent, and whose chlorinated solvent concentration has to be determined, is obtained. Intensity of Raman return at the predetermined Raman shift associated with O—H stretching region of the non-turbid aqueous solution sample is measured. The intensity of Raman return at the predetermined Raman shift associated with O—H stretching region of the non-turbid aqueous solution sample is then compared to the calibration profile for non-turbid solutions, and the concentration of the chlorinated solvent in the non-turbid aqueous solution sample is determined.

Also disclosed is a method for determining concentration of a chlorinated solvent in a turbid aqueous solution sample containing the chlorinated solvent. The method includes providing a set of non-turbid aqueous chlorinated solvent calibration solutions. Each of the non-turbid calibration solutions includes solutions of water and a chlorinated solvent and each non-turbid calibration solution has a concentration of the chlorinated solvent within a predetermined concentration range. Further, at least two of the chlorinated solvent calibration solutions in the set have different concentrations of the chlorinated solvent within the predetermined concentration range. The intensity of Raman return at a predetermined Raman shift associated with O—H stretching region of water for each of the non-turbid aqueous chlorinated solvent calibration solutions is measured. A calibration profile for non-turbid solutions is then developed relating chlorinated solvent concentrations of the non-turbid aqueous chlorinated solvent calibration solutions in the set to these measured intensities. The turbid aqueous solution sample, which contains the chlorinated solvent, and whose chlorinated solvent concentration has to be determined, is obtained. Intensity of Raman return at the predetermined Raman shift associated with O—H stretching region of the turbid aqueous solution sample is measured. A turbidity correction is made to the measured intensity of Raman return at the predetermined Raman shift associated with O—H stretching region of the turbid aqueous solution sample to obtain a turbidity-corrected intensity of Raman return at the predetermined Raman shift associated with O—H stretching region of the turbid aqueous solution sample. The turbidity-corrected intensity is then compared to the calibration profile for non-turbid solutions, and the concentration of the chlorinated solvent in the turbid aqueous solution sample is determined.

Another method for determining concentration of a chlorinated solvent in a turbid aqueous solution sample containing the chlorinated solvent is disclosed. The method includes providing a set of turbid aqueous chlorinated solvent calibration solutions. Each of the turbid calibration solutions includes solutions of water and a chlorinated solvent and each turbid calibration solution has a concentration of the chlorinated solvent within a predetermined concentration range. Further, at least two of the chlorinated solvent calibration solutions in the set have different concentrations of the chlorinated solvent within the predetermined concentration range. Also, each of the turbid calibration solutions has a turbidity value in a predetermined turbidity range. Intensity of Raman return at a predetermined Raman shift associated with O—H stretching region of water for each of the turbid aqueous chlorinated solvent calibration solutions is measured. A calibration profile for turbid solutions is then developed relating chlorinated solvent concentrations of the turbid aqueous chlorinated solvent calibration solutions in the set to these measured intensities. The turbid aqueous solution sample, which contains the chlorinated solvent, and whose chlorinated solvent concentration has to be determined, is obtained. Intensity of Raman return at the predetermined Raman shift associated with O—H stretching region of the turbid aqueous solution sample is measured. The intensity of Raman return at the predetermined Raman shift associated with O—H stretching region of the non-turbid aqueous solution sample is then compared to the calibration profile for turbid solutions, and the concentration of the chlorinated solvent in the turbid aqueous solution sample is determined.

BRIEF DESCRIPTION OF DRAWINGS

While some of the figures shown herein may have been generated from scaled drawings or from photographs that are scalable, it is understood that such relative scaling within a figure are by way of example, and are not to be construed as limiting.

DETAILED DESCRIPTION

Figure 1:
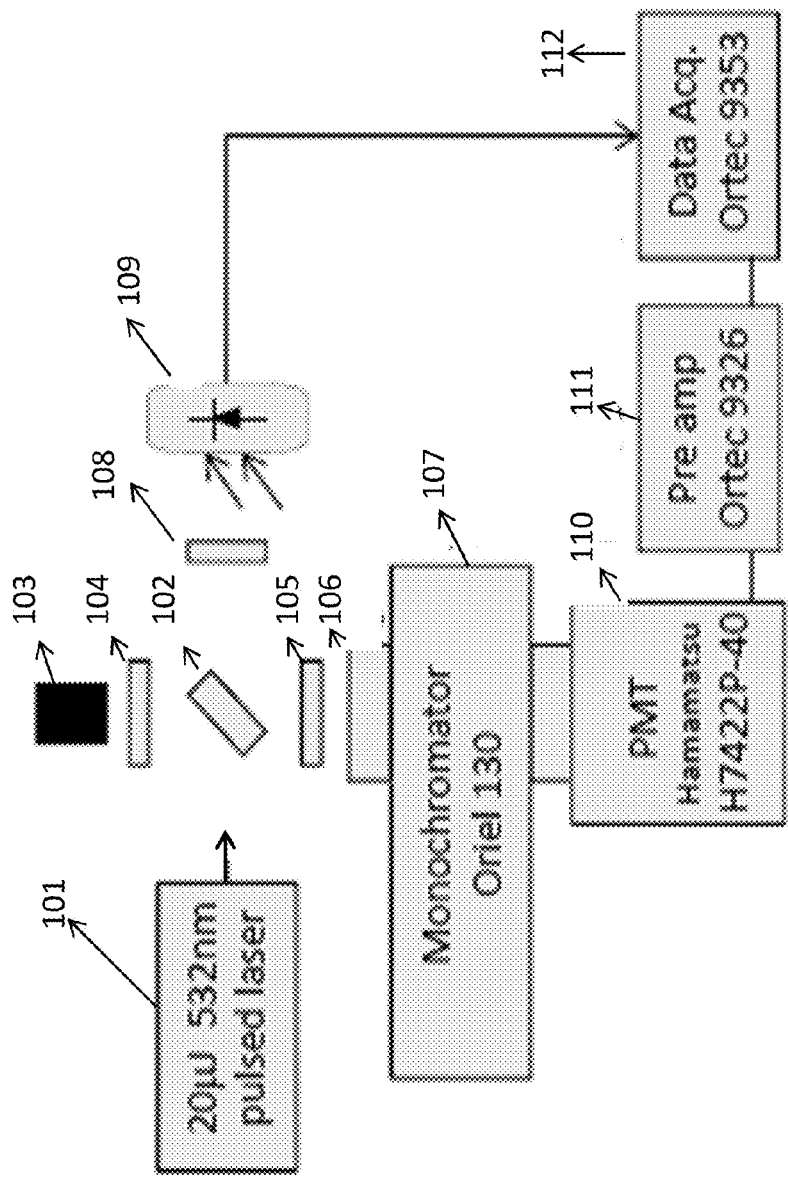
FIG. 1 is a schematic representation of a 20 µJ Raman measurement system.

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended, such alterations and further modifications in the illustrated device, and such further applications of the principles of the disclosure as illustrated therein being contemplated as would normally occur to one skilled in the art to which the disclosure relates.

Results demonstrating the method and usefulness of the disclosure are obtained using a research-oriented open-path variation of a closed-path fiber optically coupled Time-Resolved Raman Spectroscopy (TRRS) system specifically designed for application in field settings. The system trades-off lower power and longer sampling times for reduced cost, simple reconfigurability, and the ability to manage multiple environmental interferences (e.g., fluorescence, turbidity, soil-solution interface). U.S. Pat. No. 8,325,337 issued to Joseph V. Sinfield and Oliver Colic on Dec. 4, 2012, the contents of which are incorporated herein by reference in their entirety, describes open- and closed-path system configurations for TRRS. The system as employed herein consists of eight primary components as shown in the schematic representation of the time-resolved Raman spectroscopy measurement system as shown in FIG. 1.

Referring to FIG. 1, the tests and measurements leading to this disclosure were performed with an open-path 532 nm 20 µJ pulsed laser (2 kHz repetition rate; ~0.4 ns pulse duration, Teem photonics PNG-002025-100). Here the 20 µJ excitation beam 101 is directed to an Ø 25.4 mm dichroic laser beam filter (Edmund Optics) at 45 degree angle of incidence 102 which directs the excitation energy into an optical train that focuses the energy on a sample cuvette 103. Within the optical train a Ø 45 mm AR aspheric lens 104 with Numerical Aperture (NA) 0.612 (Thorlabs) focuses the excitation on the sample and serves as a collection and focus optic for the 180 degree back scattered Raman photons from the sample back through the dichroic filter 102 to a Ø 50.8 mm AR achromatic doublet lens 205 (Thorlabs) with NA of 0.17. The achromatic lens in turn focuses Raman photons on the entrance slit of a monochromator 107 (Oriel 130 ⅛ m, with flat-ruled 1200 lines/mm grating blazed at 500 nm). A 532 nm Ø 25.4 mm long-pass filter is placed at the monochromator entrance slit 106 to eliminate source wavelength background. Energy passing directly through the dichroic filter is focused through a convex lens 108 and used to create a data acquisition trigger via a photodiode 109. Light passing through the monochromator is observed using a photomultiplier tube (PMT) (Hamamatsu H7422-40P) 210 operated in a photon counting mode. The PMT is observed via an impedance matched link to a pre-amplifier (Ortec 9326, operated at a gain of 20×) 111 and a 100-ps binned comparator (Ortec 9353) 112. For all experiments performed with this system, spectra were collected with 25 µm slits, a step size of 0.1 nm, and 120 s observation time per wavelength. Other settings are possible.

Spectrometric grade trichloroethylene (TCE) (purity>99.5%) obtained from Alfa Aesar was used as received in several experiments leading to this disclosure. Trichloroethylene ($C_2HCl_3$) is denser than water, slightly soluble and volatile. Its properties are as follows: density of 1.465 g/mol; a relative solubility of 1.2 g/L at 25° C.; $K_\alpha$=2.03-2.70; a vapor pressure of 74 mm Hg and a Henry's law constant of 0.011 atm-m$^3$/mol. All non-neat test solutions were prepared using TCE and distilled, deionized water. Aqueous samples were prepared at room temperature 24.5-26.7° C. in a 40-ml amber colored glass vial with a Teflon-coated silicone rubber septa that was sealed and screwed in place with a cap. The 40 ml bottles were filled with deionized water to a capacity of 30 mL and then neat TCE was injected at the base of the water filled vial with the use of a disposable pipette to help ensure that no bubbles were introduced in the process. The injection was stopped when the supernatant water reached the brim of the vial. The vials were then capped and sealed immediately to avoid headspace and prevent loss due to vaporization. These vials were then gently manually shaken and allowed to settle to equilibrium for at least three days.

The aqueous equilibrium trichloroethylene concentration served as a stock solution for further dilution to lower aqueous concentrations and these diluted samples were tested immediately to minimize losses due to volatilization and degradation. To prepare dilute concentrations, the aqueous equilibrium solution of TCE was extracted through the use of a syringe and injected into a closed vial containing deionized water in an appropriate volume needed to make that particular concentration based on a molarity mass balance ratio, see Equation 1.

$$C_i V_i = C_f V_f \quad \text{(Equation 1)}$$

The concentration and volume are represented by C and V, while the subscripts i and f represent the initial and final target solution respectively, with consistent volumetric units.

Test samples designed to simulate biodegradation in a field environment were prepared by first cultivating an anaerobic microbial population within a natural saturated soil sample. Soil for the experiment was obtained from a forested area near the intersection of Cherry Lane and McCormick in West Lafayette, Ind. and was characterized as silty clay that plots in the CL-ML region of a soil plasticity chart. It has a brownish gray color and a plastic and liquid limit of 8% and 26%, respectively. The soil was used as obtained from the site without any modifications.

The soil was placed in a flask and saturated with a buffered solution and fed a solution consisting of of glucose ($C_6H_{12}O_6$), methanol ($CH_3OH$), and ethanol ($C_2H_5OH$). The soil was incubated in a foil covered (opaque to light) sealed vessel and monitored for microbial activity as evidenced by steady production of $CO_2$ and $CH_4$ gases. Glucose is easily and rapidly degradable by a diverse array of microbes, while ethanol and methanol are easily catabolized by acetogenic and methanogenic bacteria respectively, thus ensuring a rapid onset of anaerobic and methanogenic conditions needed to simulate groundwater conditions found at many contaminated sites. A steady pH of 7.2 was maintained daily and when needed the pH was adjusted with small additions of a concentrated buffer stock (per 100 ml; ammonium chloride ($NH_4Cl$) 100 mg, potassium dihydrogen phosphate ($KH_2PO_4$) 500 mg and potassium hydrogen phosphate ($K_2HPO_4$) 2000 mg). The microbial bioassay created (supernatant liquid and slurry soil composition) was extracted using a pipette and combined with aqueous solutions of TCE on a volumetric basis, shaken, and allowed to equilibrate evenly in a Teflon sealed screwed cap vial. Extracts of the supernatant liquid were then used for testing the instrument performance in a simulated biologically active and complex environment.

Trichloroethylene concentrations were validated by USEPA Method 8010 using a Stanford Research Instruments (SRI) Environmental Gas Chromatograph (GC 8610C chassis) equipped with a Photo Ionization Detector (PID) in series with a combination Flame Ionization Detector (FID) and a Dry Electrolytic Conductivity Detector (DELCD). The PID detector responds to compounds, whose ionization potential is below 10.6 eV, including aromatics and chlorinated molecules with double carbon bonds (TCE has an ionization potential of 9.45 eV). The FID detector responds to the hydrocarbons in the sample while the DELCD selectively detects the chlorinated and brominated compounds in the FID exhaust. Unless stated otherwise, all spectra were collected with a 25 μm slit size and an optical resolution of 4 $cm^{-1}$ (~0.1 nm step size) with a sampling time of 120 sec per wavelength. For simple aqueous solutions, a five point analysis procedure was applied for all studied frequencies, which included observation of Raman returns at the line of interest, two additional points immediately adjacent to the line, and two more points on either side of the peak within the baseline noise. These observations represent a single complete sampling process, and provide a robust assessment of the Raman contribution relative to background noise.

The information obtained from the TRRS analysis can be portrayed in an x-y plot of the Raman intensity (counts) vs. Raman shift ($cm^{-1}$). Total counts were obtained by the progressive summation of returned Raman photon counts from the output of the photomultiplier tube (PMT) as observed by the time digitizer in one thousand 100 picosecond time bins that collect counts following incidence of the laser pulse at the sample. Signal to Noise Ratio (SNR) is defined as the average of the counts at the Raman peak (i.e. counts at which a given Raman vibrational mode occurs) minus the baseline divided by the standard deviation of the peak counts. Spectral subtraction, baseline removal, peak identification and smoothing were performed.

Raman spectroscopy is an analytical technique that has seen broad application in research and industrial settings for the analysis of solids, liquids and gases. In this technique a monochromatic light source (typically a laser) is directed toward a target and inelastic photon-molecule collisions are observed. The inelastic collisions—or Raman scattering events—result from roughly 1 out of every 10 million incident photons and take place on a time scale on the order of $10^{-12}$ seconds.

The inelastically scattered photons display a change in energy from their initial state that can be described by the equation below:

$$\Delta E = E_o - E_{vib} \quad \text{(Equation 2)}$$

(Subscript o and vib represent incident and scattered photons, respectively)
where,
E=hv=hc/λ
h is Planck's constant
v is the frequency of the light
c is the speed of light
λ is the wavelength of light The difference in energy, ΔE, is equivalent to the energy transferred between the incident photon and the sample, and corresponds to the vibrational and rotational energy states of the target molecule bonds. A reduction in energy of scattered photons leads to a reduction in frequency (increase in wavelength) known as a Stokes shift, and this is the basis for most conventional Raman spectroscopy. Alternatively, an increase in energy of the scattered photons can occur when an already excited bond transfers energy to the incoming incident photons causing an increase in the scattered photons' energy, and thus frequency. This phenomenon is called an anti-Stokes shift, but is not commonly observed. Conventionally these changes in energy, or shifts, are reported in units of wavenumber ($cm^{-1}$) with reference to the wavelength of the incident light. The spectrum of observed scattered frequencies, known as the Raman spectrum, thus relates to the bonds in a molecule, and the relative intensity of lines in the spectrum is consistent with molecule stoichiometry. In time-resolved Raman spectroscopy, a pulsed, rather than a continuous wave, laser is employed to interrogate a sample and scattered photons are collected only during a brief period of time from the onset of the incident pulse until a point in time prior to the onset of significant fluorescence (if present). Time gating is thus typically performed on a time sale on the order of $10^{-9}$ seconds, or faster. Observations of scattered photons are then typically accumulated via photon counting techniques over repeated cycles of the laser pulse to enhance signal to noise ratios and develop a robust Raman spectrum.

Chlorinated solvents are fundamentally composed of single, double or triple carbon-carbon bonds, carbon-chlorine bonds (C—Cl) and carbon-hydrogen bonds (CH). As explained above, bonds are associated with characteristic molecular vibrations and hence Raman frequencies. Previous studies have shown that C=C bonds give rise to characteristic shifts around the 1580-1664 $cm^{-1}$ region. Further, vibrations involving CH bonds give rise to vibrational frequencies that are characterized by molecular stretching identified at the 2840-3000 $cm^{-1}$ regions in a Raman spectrum. Shifts in groups at 730-840 $cm^{-1}$ and 1240-1360 $cm^{-1}$ are attributed to wagging and stretching of CH bonds, respectively. The presence of halogens such as chlorine atoms are identified by shifts in the frequency region of 550-760 $cm^{-1}$. In addition, skeletal deformations associated with the C—Cl bonds relate to frequencies at 381 $cm^{-1}$ and 274 $cm^{-1}$.

These characteristic Raman vibrational groups for C=C, CCl and CH were clearly observed in the Raman spectra of six neat chlorinated compounds (trichloroethylene (TCE), tetrachloroethene (PCE), 1,1,2,2 tetrachloroethane (PCA), 1,1,1 trichloroethane (1,1,1 TCA), dichloromethane (DCM), and Cis 1,2 dichloroethene (cis 1,2 DCE)) tested using the TRRS system, confirming system performance that is consistent with literature. Although there are a wide range of chlorinated solvent DNAPLs encountered in the field, as alluded to above, research in this effort was focused on trichloroethlyene (TCE). This was primarily due to the limited availability of substantial quantities of other chlorinated solvents in neat form, which can be traced to the move by regulatory bodies like the United States Environmental Protection Agency (USEPA) to gradually minimize or eradicate these carcinogenic chemicals. Thus work here focused on a more detailed analysis of the Raman spectrum of trichloroethylene to highlight "fingerprint" frequencies which are unique to TCE. Overall, the characteristics of the trichloroethylene Raman spectra obtained using the 20 μJ system are consistent with standard assigned vibrational modes presented in literature. In FIG. 1, graphs (a), (b), and (c) represent typical Raman Spectra of neat TCE, water, and 600 ppm TCE aqueous solution, respectively. In this context and specification "neat TCE" is meant and generally understood by those skilled in the art to mean TCE without any additional solvent and with purity generally found in reagent grade TCE.

Figure 2:
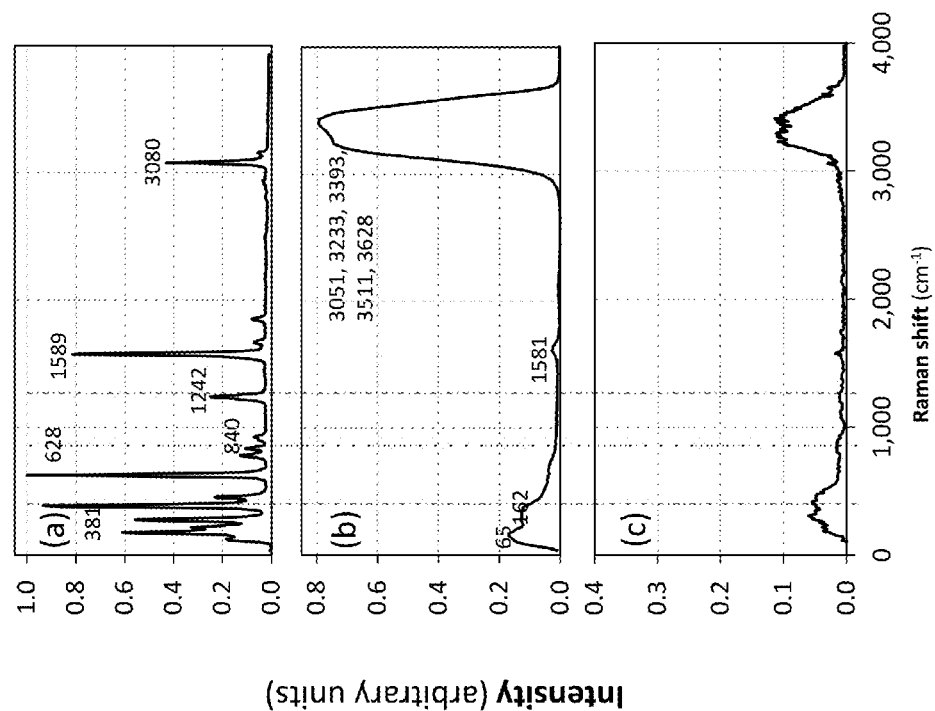
FIG. 2 is a representation of characteristic Raman Spectra of neat TCE, water, and 600 ppm TCE aqueous solution.

The Raman spectrum of water is characterized by the intramolecular O—H stretching modes from 2700-3800 cm$^{-1}$. (Note: O—H stretching is sometimes written as OH stretching. Thus, in this specification, OH stretching and O—H stretching are used interchangeably.) This broad response can be deconvolved into five peaks, 3051, 3233, 3393, 3511, 3628 cm$^{-1}$. Deconvolving (i.e. separating into contributing parts) in this context refers to separating the aggregate Raman water signal over the range of 2700-3800 cm$^{-1}$ into the contributions from the five primary vibrational modes that comprise this signal. Further characteristic vibrations have been identified at the 1581 and 1640 cm$^{-1}$ Raman shift, which are associated with the bending modes of O—H bonds. A third set of peaks can be observed at the 65 and 162 cm$^{-1}$ frequencies. The former is linked to O—O—O bending, while the latter is attributed to the O—O stretching along the O—H—O or hydrogen bond direction. In FIG. 2, graph (b) displays a TRRS scan of water obtained using the open path 20 μJ laser configuration, with similar experimental settings to the TCE spectrum, which reflects all of the vibration modes outlined above.

Experiments were performed to directly and indirectly assess TCE levels in aqueous solution. Observations from each approach are described in detail below.

In the early seventies when it was first illustrated that Raman spectroscopy could be used for the detection of pollutants in water, there was a surge in the application of Raman spectroscopy for environmental analyses. This is because, unlike other spectroscopic techniques such as Infra-Red (IR) spectroscopy which are limited because water absorbs IR radiation. Raman spectroscopy is tolerant of water because water is generally a weak Raman scatter and even water's stronger vibrational modes are notably displaced in the frequency domain from those of most target analytes.

When a single compound is analyzed in water, the observed spectrum is made up of signals arising from Raman scatter from the analyte, water, and various forms of background (for example elastic scattering, signatures from impurities, and, of course, electrical noise). The magnitude of the analyte signal is generally linearly proportional to the analyte concentration in the water, based on the classic equation:

$$IR = I_{vib} \sigma C dz K \qquad \text{(Equation 3)}$$

Where IR=measured Raman intensity, in photons per second;
$I_{vib}$=laser intensity, in photons per second;
σ=absolute Raman cross section, in cm$^2$ per molecule
dz=sample path length, in cm;
C=concentration, in molecules per cm$^3$
K=measurement parameter (to account for experimental parameters such as optical collection efficiency and optical transmission of the Raman spectrometer which is unitless and instrument specific, determined from the optical configuration).

Experiments in this effort were initiated with direct observation of the Raman features of TCE in aqueous solution. Scans of TCE in water at solubility (i.e., approximately 1200 ppm) were first performed to obtain a baseline of the TCE Raman frequencies observable in the aqueous system and to determine their relative intensities. As illustrated in FIG. 2, which compares Raman signatures of (a) neat TCE, (b) water, and (c) TCE in aqueous solution at 600 ppm, TCE Raman lines at 381 (δ skeletal), 628 (vCCl), 780 (δCH), 840, 930 (CCl), 1242 (CH), 1589 (C=C) and 3080 cm$^{-1}$ (vCH) were observed in neat solution. The Raman signature for TCE in aqueous solution, however, is notably different from that of the neat compound, with clear suppression of C—Cl vibrational modes in the mid-frequencies in the aqueous signature relative to that for the neat compound. These changes in Raman scatter can most likely be attributed to intermolecular interaction between H atoms in water and the C—Cl groups of the TCE molecules, which, by creating regions of hydrophobic hydration around the Cl atoms, weaken the C—Cl vibrations, as first put forward in literature. In addition, the intensity of C—H group frequencies are likely impacted by the formation of hydrogen bonds with proximal water molecules as discussed in more detail below.

In order to assess direct detection limits for TCE with the TRRS system in a simple aqueous solution laboratory setting (noting that detection limits are inevitably a function of the system excitation power, transfer function, and noise signature), a subset of the observable TCE Raman vibrations were selected for further analysis that are both present in aqueous solution and do not overlap with primary water functional group vibration modes, namely 381, 840, and 1242 cm$^{-1}$.

Figure 3:
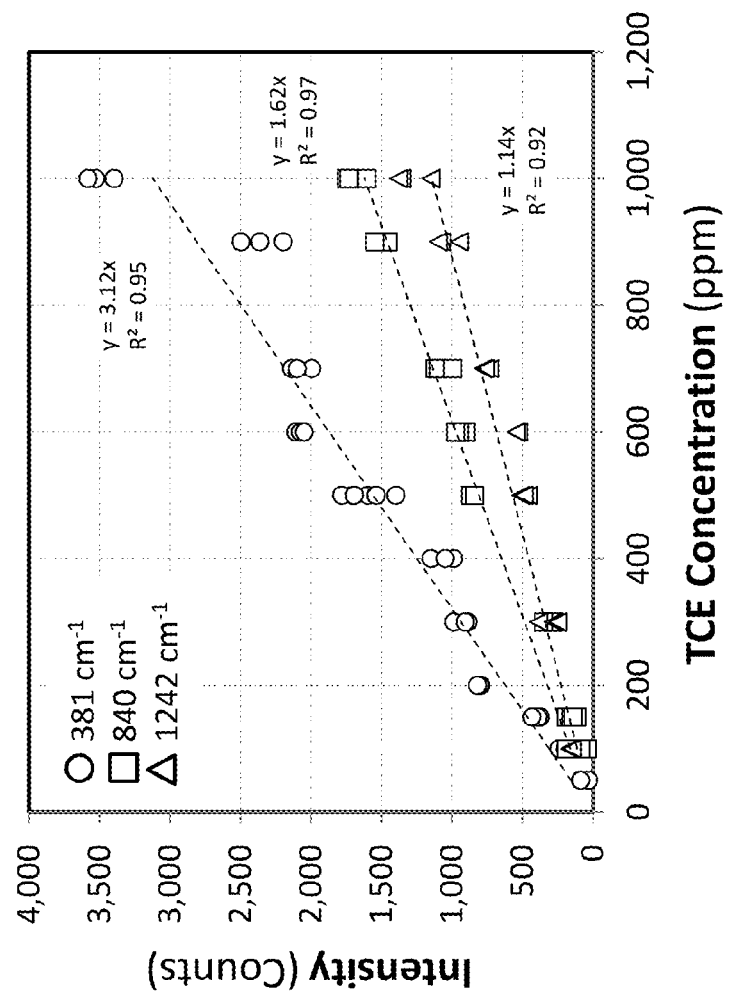
FIG. 3 is a graph of Raman intensity vs. TCE concentration in aqueous solution at 381, 840 and 1242 $cm^{-1}$.

The relationship between the intensity of the Raman return (in counts) at each of these lines to the concentration of TCE in solution was then studied over a range of concentrations. Verification of analyte concentration for all tests was performed using a GC-FID-DELCD in series combination. For all tests, scans were performed using a step size of 0.1 nm with a sampling time of 120 sec per wavelength. At least three scans were performed at each line of interest, for each concentration studied. Raman peak heights were determined utilizing, as a non-limiting example, the classic Gaussian-Lorentzian (G-L) fitting method. The results of these analyses are depicted in FIG. 3 for vibrations at 381, 840, and 1242 cm$^{-1}$, respectively.

Detection limits, defined as the concentration observable at an SNR of 3, where SNR is defined as the average of the peak counts at the Raman line minus the baseline divided by the standard deviation of the peak counts, are approximately 70 ppm, 110 ppm, and 135 ppm, for the vibrations at 381, 840, and 1242 cm$^{-1}$, respectively. While not representative of drinking water maximum contaminant levels, these detection limits are well within a range that can be useful and valuable for directional mapping of contaminant plumes, site characterization, and long term monitoring, even at the generally modest laser power of the employed system, indicating significant potential for use in environmental applications, especially given the typical contaminated site groundwater and plume TCE concentrations noted earlier.

While performing direct observations of TCE, Raman scans were carried out over an extended range of frequencies to facilitate comparison with literature. As a result, it was observed that as the concentration of TCE in solution increased, the Raman signature of water decreased in intensity, particularly in the O—H stretching region (2700-3800 cm$^{-1}$). This observation highlighted the potential to employ Raman measurements of water to indirectly infer the presence of the target analyte, or at least compounds within a chemical family similar to that of the target analyte. This approach is elaborated below.

Figure 4:
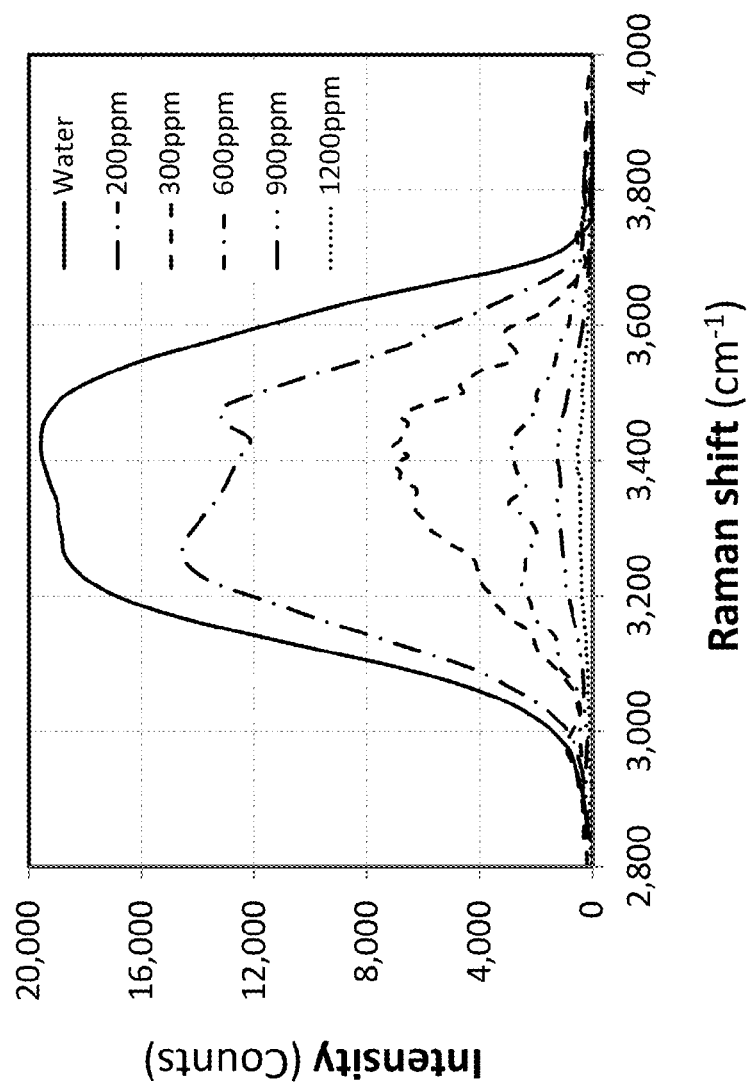
FIG. 4 is a representation of the relationship of TCE concentration in aqueous solution to the intensity of Raman vibrational modes in the O—H stretching region of water.

The Raman signature of water undergoes significant changes as the concentration of TCE in aqueous solution increases. Most notably, increases in TCE concentration drive marked reductions in the intensity of the water vibrational modes at the smaller shifts (65 and 162 cm$^{-1}$) associated with O—O—O bending, and O—O stretching along the O—H—O or hydrogen bond direction, as well as the O—H stretching region (2700-3800 cm$^{-1}$). FIG. 4 shows this effect in the O—H stretching region, which is particularly helpful because this region has little overlap with the Raman modes of chlorinated solvents. The inverse relationship between the concentration of TCE in aqueous solution and the intensity of the O—H stretching region water Raman lines is likely the result of intermolecular interaction between the TCE and surrounding water molecules. A reduction in the intensity of Raman vibrations of water can result from either of two phenomena described below.

First, it has been shown that when water is used as a solvent for small organic halogen molecules and halide salts, the hydrogen bonded tetrahedral structure of water can be weakened as the hydrogen atoms of some water molecules develop hydrogen bonds preferentially with the halogen. This interaction has been termed a "structure breaking" effect and, in very early studies, was reported to increase with increasing ionic radius of the halides. The impact of this effect has been documented by several researchers and is characterized by a moderate decrease in the Raman intensity of water vibrational lines at 65 and 170 cm$^{-1}$, corresponding to O—O—O bending, and O—O stretching along the O—H—O direction, as well as a more pronounced reduction in the intensity of the O—H stretching vibrational modes of water from 2700-3800 cm$^{-1}$.

A second potential mechanism driving the observed changes in the water Raman return stems from more recent experimental and computer simulation work that has called into question the bulk "structure breaking" phenomenon and instead links water Raman intensity reductions to electric field effects resulting from O—H . . . X (here X=Cl) interactions in the first solvation shell surrounding the solute which drive strong orientation of hydrogen atoms in the water toward the solute and potentially reduced rotational mobility of the local water molecules, rather than formation of hydrogen bonds with other water molecules.

Beyond these influences which likely contribute to a reduction in water Raman intensities, for every TCE molecule, there is one hydrogen atom within the C—H group that could offer a counter effect by driving the creation of hydrogen bonds with neighboring water molecules. However, the 3:1 ratio of Cl to H in TCE suggests that the former effects dominate the observed trends, resulting in a net decrease in the intensity of water Raman vibrations with increasing TCE concentration.

Figure 5:
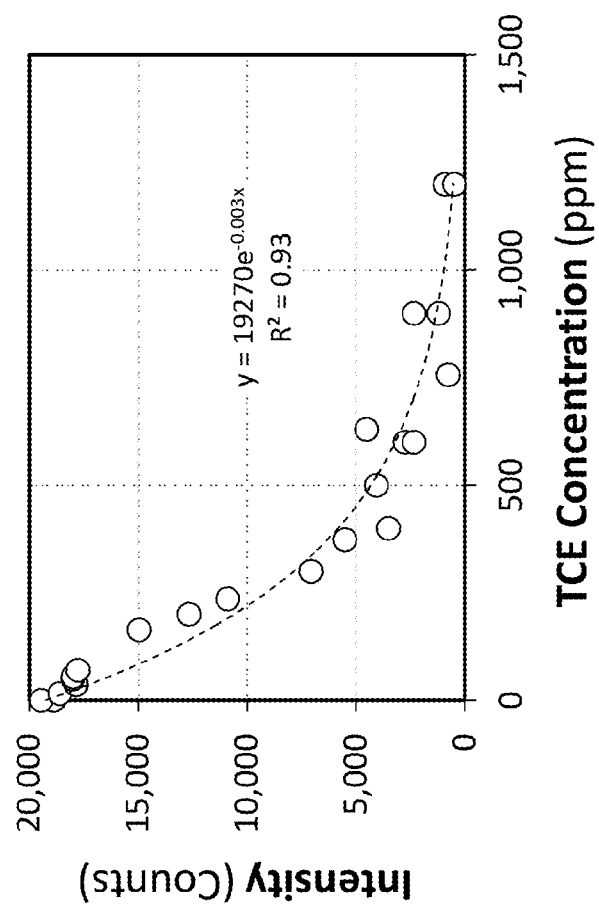
FIG. 5 is a representation of the measured relationship between water line Raman counts at 3393 $cm^{-1}$ and TCE concentration in aqueous solution.

On this basis it is possible to develop a "calibration profile" for analysis of aqueous TCE samples, in this case, relating changes in TCE concentration to changes in the intensity of the most affected vibrational modes of water. As discussed earlier, the water Raman spectrum is distinguished by broad intermolecular O—H stretching modes from 2700-3800 cm$^{-1}$, which can be deconvolved into five peaks. Here, the 3393 cm$^{-1}$ peak, which was deconvolved, was employed to develop a calibration profile used for the indirect monitoring of TCE concentration as it consistently yielded the highest SNR during TRRS measurements of TCE concentrations. The resulting calibration profile is shown in FIG. 5 which shows the measured relationship between water line Raman counts at 3393 cm$^{-1}$ and TCE concentration in aqueous solution. The profile specifically highlights the relationship between counts observed at the 3393 cm$^{-1}$ Raman line of water and the concentration of TCE in solution.

Although clearly non-linear, the calibration profile has a negative slope and is steeper than those obtained from direct observation of TCE lines, thus providing a larger "calibration factor" as in the classic characterization of a sensor. This implies that observations of the O—H stretching region of water could offer greater sensitivity to changes in TCE concentration then observation of TCE-specific lines, and thus enable improved detection limits, depending on the complexity of the solution being examined. In this simple case of a single compound solution, a detection limit of ~8 ppm is achievable, again on the basis of maintaining an SNR≥3. The ratio of the direct to indirect detection limits is 70/8=8.7, which implies 8.7× greater sensitivity to changes in TCE concentration.

While the phenomena described above which likely account for the inverse relationship between water line Raman intensities and TCE concentration have been known for quite some time, the authors believe that the work presented herein highlights a potentially unique use of the effect as a sensing mechanism for chlorinated contaminants, particularly in environmental applications. Although halogens other than chlorine (i.e, F, Br, I), are known to cause a similar effect to a lesser or greater extent and a broad array of "structure breaking and making" compounds have been observed few of these alternate drivers of the water Raman intensity are likely to be encountered in most natural settings, particularly at the depths where DNAPLs are often found. It has been demonstrated that chlorine has the greatest adverse effect on water Raman intensities among Group VII elements. Thus, even if other influences were present but as part of the natural "background" signature, a reduction in the intensity of the water signature at a given site location relative to the water signature from a related but uncontaminated location would be indicative of water contamination with high likelihood. With this in mind, careful observation of water Raman signatures in site exploration and monitoring efforts can offer a valuable and more sensitive indication of aggregate chlorinated solvent contamination than direct observation of the target compounds.

Recognizing that successful field application of a TRRS monitoring system will require the capability to make effective Raman observations in the field in an environment much more complex than simple aqueous solutions; tests were also performed on samples that simulated an environment representative of a field scenario. These samples, which contained water, TCE in aqueous solution, soil particles, and microbes capable of biodegradation, represented the supernatant turbid liquid separated from a natural soil slurry and were prepared as discussed previously.

Figure 6:
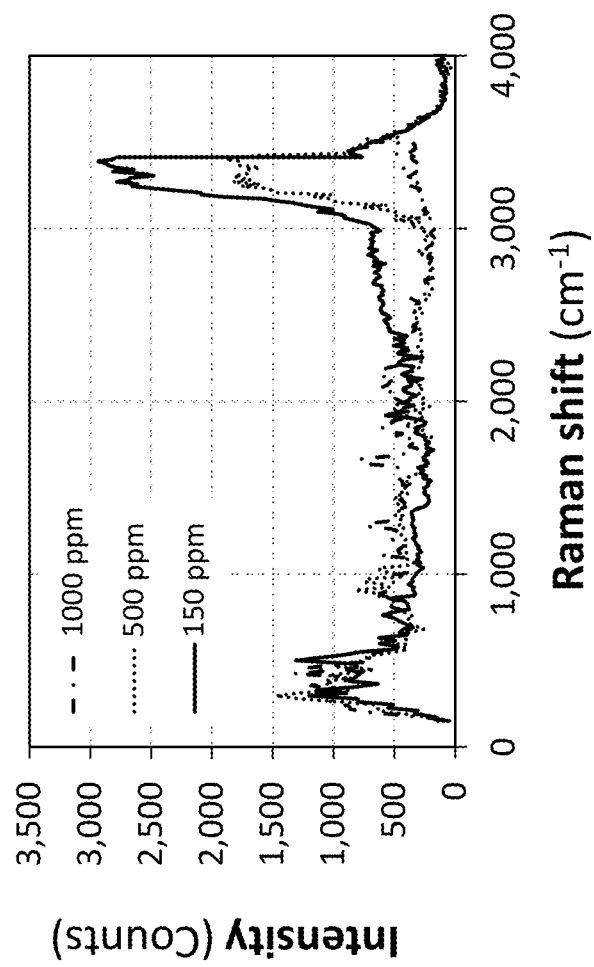
FIG. 6 shows Raman spectra of TCE doped turbid supernatant bioassay.

For the study of simulated degradation samples, TRRS scans (20 µJ open path configuration, 120 s per wavelength, step interval of 0.1 nm) were run over a broad Raman shift range for turbid supernatant doped to contain 150, 500, and 1000 ppm TCE by volume. The results of these scans are shown in FIG. 6. FIG. 6 shows Raman spectra of TCE doped turbid supernatant bioassay. Referring to FIG. 6, it is apparent that the observed Raman signature is quite complex. While it is not the intent of this analysis to study the full breadth of constituents in these samples, contributions to the Raman spectrum of this complex sample can be anticipated from an array of sources. The elevated spectral range between 900-2000 cm$^{-1}$ may be attributed to group frequencies usually found in soil constituents, with spectral ranges between 950-1170 cm$^{-1}$ typically pertaining to C—O stretching of polysaccharides; 1450-1650 cm$^{-1}$ to COO- stretching, and 1630-1750 cm$^{-1}$ to C=O stretching. Glucose, which is known to be present in the sample, can be anticipated to provide Raman returns appearing in the 400-550 cm$^{-1}$ range (most notably 397, 424, and 543 cm$^{-1}$) which have been attributed to the skeletal vibrations δ(C—C—C), δ(C—C—O), and δ(C—O), respectively, and in the 850-950 cm$^{-1}$ range (notably 868 and 916 cm$^{-1}$) due to the ν (C—C) and δ (C1-H1) vibrations Vibrational bands between 1000-2000 cm$^{-1}$ are generally related to contributions from ν(C—C) and ν(C—O) stretching vibrations in soil functional groups and the microbe feed. The Raman spectrum of the supernatant liquid clearly showed the distinctive intramolecular O—H stretching modes of water from regions 2700-3800 cm$^{-1}$. Contributions from the Raman vibrational modes of TCE are not obviously discerned upon visual examination. In addition, a non-time-gated analysis of the photon returns also confirmed that there is some contribution of fluorescence in the baseline of the signature, likely from fulvic and/or humic compounds present in the natural soil.

Spectral analysis was also undertaken on the turbid supernatant spectra. A spectral background subtraction was performed, after which a peak fit utilizing the Gaussian-Lorentzian (G-L) fitting method was explored to locate TCE peaks 381, 840 and 1242 cm$^{-1}$. While peak intensity and concentration were observed to be generally correlated, these trends were not as robust as those associated with indirect monitoring. Hence subsequent analysis was focused on the indirect measurement of the 3393 cm$^{-1}$ mode of water which displayed a distinct peak and change in intensity due to the presence of chlorinated solvents (see FIG. 6). Tests were performed to obtain these indirect measurements of TCE at seven aqueous TCE concentrations (150, 250, 400, 500, 600, 800, 1000 ppm) in the turbid supernatant bioassay. The turbidity value for each sample was also measured before TRRS analysis using a turbidimeter, and ranged from 20 to 150 NTU. (Note: NTU's are Nephelometric Turbidity Units. NTUs provide a standardized measure of the extent to which white light is scattered at an angle of 90° from the direction of an incident beam by particles suspended in a liquid relative to the same effect observed in a standard solution containing the polymer reaction byproduct of hydrazine sulfate and hexamethylenetetramine, in accordance with Environmental Protection Agency (EPA) Method 180.1.)

Figure 7:
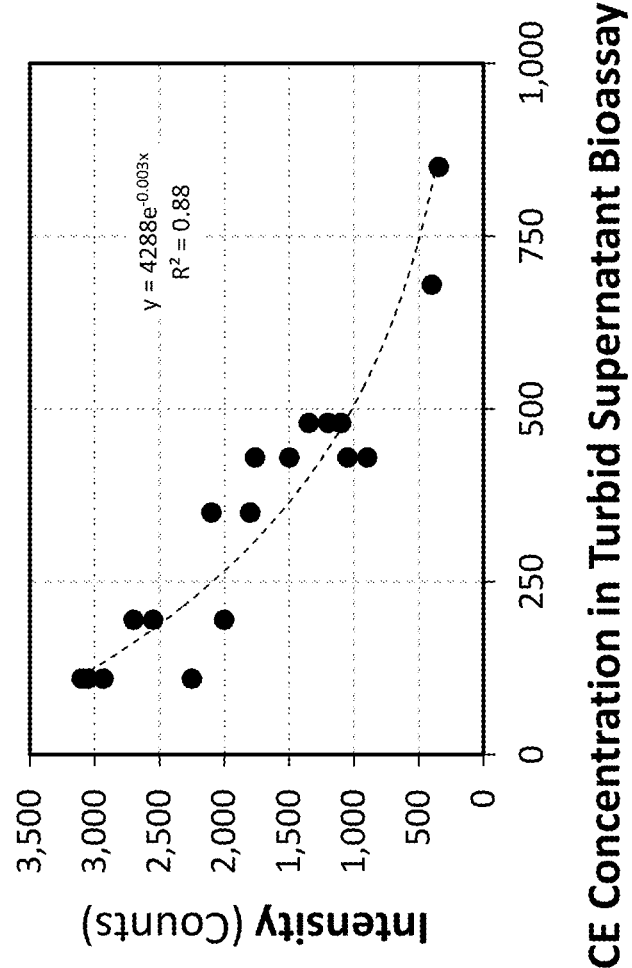
FIG. 7 shows the relationship of water line Raman counts at 3393 cm$^{-1}$ to the TCE-concentration in simulated field samples consisting of doped turbid supernatant bioassay

The concentrations of the supernatant TCE-bioassay solutions were verified using the GC-FID-DELCD and it was noticed that TCE concentrations in the supernatant were 12-26% lower than planned volumetric concentrations. This reduction can likely be attributed to the partitioning ($K_d$) of the TCE on to the organic carbon fractions ($f_\propto$) of the soil. An $f_\propto$ for the investigated soil was determined to be 2.21%, leading to a $K_d$ value of 3.67 for TCE, which is consistent with reported values of the distribution coefficient of TCE in the field, and, based on the mass of soil in the supernatant, could readily account for the discrepancy between intended prepared concentrations and those evident in the supernatant liquid fraction. Given this variation, the TCE concentration in the supernatant liquid as verified by GC-FID-DELCD analyses was then compared to the Raman intensity of the O—H stretching water vibration at 3393 cm$^{-1}$, also obtained on tests of the supernatant, as shown in FIG. 7. FIG. 7 shows the relationship of water line Raman counts at 3393 cm$^{-1}$ to the TCE-concentration in simulated field samples consisting of doped turbid supernatant bioassay. Although the absolute magnitudes of these observations vary relative to those presented in FIG. 6, which can be attributed to the highly turbid nature of the studied samples, the results uphold the form of inverse relationship discussed earlier relating chlorinated solvent concentration to observable changes in the O—H stretching vibrational modes of water, even in complex samples representative of field conditions.

The above detailed description contrasts direct and indirect means to assess TCE levels in aqueous solution using time-resolved Raman spectroscopy. The TRRS system employed herein was able to directly detect TCE at aqueous concentrations as low as 150 ppm in simple aqueous solution by monitoring the 381 cm$^{-1}$ Raman line corresponding to the δCCl vibrational mode. This level of sensitivity, achieved with the outlined embodiment of the Raman system, while far from drinking water maximum contaminant limits, may have value in certain field monitoring applications such as plume delineation, warning of contaminant release, or the design of tailored monitoring approaches. Additional observations highlighted that the intensity of water Raman vibrations in the O—H stretching region are inversely related to TCE concentration in aqueous solutions following a negative exponential relationship. At comparable laser power and test parameters, observation of the O—H stretching water Raman line provided nearly a 10× improvement in detection level relative to direct observation of the strongest observable TCE Raman line in simple aqueous systems (here 381 cm$^{-1}$), with observation of the 3393 cm$^{-1}$ O—H stretch providing evidence of the presence of the chlorinated solvent TCE in water at aqueous concentrations as low as ~8 ppm. Additional tests performed on simulated biodegraded field samples reaffirmed the potential to employ monitoring of the O—H stretch Raman vibrational modes for indirect monitoring of TCE even in complex samples containing TCE, water, natural suspended soil particles, and microbes.

The interrelationship between chlorinated solvent presence and the vibrational modes of water suggests that Raman monitoring of the O—H stretching band of water can serve as a valuable indication of the presence of aggregate chlorinated solvent contamination in aqueous systems, which could be more sensitive and robust than direct monitoring of chlorinated solvent Raman peaks. Although the observations reported herein are promising, it is important to note several limitations to application of the findings. First, the monitoring method put forward does not, as of yet, offer an opportunity to differentiate different chlorinated compounds or their daughter products that might be encountered in the field (e.g., vinyl chloride, or ethylene chloride in the case of TCE). Further, a number of chemicals are also known to influence the O—H stretching band of water, such as glucose and urea, which could potentially introduce errors in field analyses. However, these compounds are not likely to be encountered at ground depths associated with chlorinated solvent contamination. Overall, the results presented herein offer promising support for continued exploration of Raman analysis as a means to facilitate chlorinated solvent monitoring.

It should be noted that in the special case of having only two chlorinated solvent solutions for a calibration, the calibration profile will be a straight line, as is obvious for those skilled in the art. When more than two chlorinated solvents are used for calibration, the calibration profile is generally non-linear, though linear relationships may be observed in some cases, such as when the concentration ranges for the solutions is narrow.

Consistent with the description above, a method for determining the concentration of a chlorinated solvent in a non-turbid aqueous solution sample containing the chlorinated solvent through Raman spectroscopic observation of the vibrational modes of water can now be described. The term non-turbid usually refers to a level of turbidity below which the influence of any suspended particles has negligible implications on the intensity of the observed Raman signals for a particular application. Before using the method, it should be verified that the aqueous solution sample containing the chlorinated solvent is non-turbid. The method begins with providing or obtaining a set of non-turbid aqueous chlorinated solvent calibration solutions which are solutions of water and a chlorinated solvent. In this set, each calibration solution has a chlorinated solvent concentration falling in a predetermined concentration range. The set should contain at least two calibration solutions with different chlorinated solvent concentrations falling within the predetermined concentration range. This predetermined concentration range can be based on any prior information about the range concentrations expected in the solution sample. Then intensity of Raman return at a predetermined Raman shift associated with O—H stretching region of water for each of the plurality of non-turbid aqueous chlorinated solvent calibration solutions is measured. The predetermined Raman shift can be based on preliminary experiments in which Raman returns at different Raman shifts associated with O—H stretching region of water are measured, and specific Raman shift can be chosen based intensity, measurement sensitivity and error minimization. Thus, a calibration profile for non-turbid solutions is then developed relating chlorinated solvent concentrations of the plurality of the non-turbid aqueous chlorinated solvent calibration solutions in the set to the measured intensities of Raman return at the predetermined Raman shift associated with O—H stretching region of water for each of the non-turbid aqueous chlorinated solvent calibration solutions in the set of non-turbid aqueous chlorinated solvent samples. A non-turbid aqueous solution sample, the chlorinated solvent concentration of which has to be determined, containing the chlorinated solvent is then obtained. Then, intensity of Raman return at the predetermined Raman shift associated with O—H stretching region of the non-turbid aqueous solution sample is measured. This measured intensity of Raman return at the predetermined Raman shift associated with O—H stretching region of the non-turbid aqueous solution sample is then compared to the calibration profile calibration profile for non-turbid solutions described above. By this comparison, concentration of the chlorinated solvent in the non-turbid aqueous solution sample is determined.

In some situations, the aqueous solution sample, whose chlorinated solvent concentration has to be determined, may be turbid. Turbidity is a measure of the loss of optical transparency of a medium resulting from the presence of suspended solids or other interfering matter, which can limit the overall sensitivity of optical spectroscopic methods and make it challenging to perform quantitative analysis. Turbidity is measured by various methods known to those skilled in the art and is typically measured in NTUs (Nephelometric Turbidity Units). NTUs provide a standardized measure of the extent to which white light is scattered at an angle of 90° from the direction of the incident beam by particles suspended in a liquid relative to the same effect observed in a standard solution containing the polymer reaction byproduct of hydrazine sulfate and hexamethylenetetramine, in accordance with Environmental Protection Agency (EPA) Method 180.1, and are a standard measure of water quality in environmental science.

If the aqueous solution sample, whose chlorinated solvent concentration has to be determined, is turbid, the method outlined above for non-turbid aqueous solution samples has to be modified to apply a turbidity correction to the intensity of Raman return at the predetermined Raman shift associated with O—H stretching region of the turbid aqueous solution sample, and the turbidity-corrected intensity is compared to the calibration profile to determine concentration of the chlorinated solvent in the turbid aqueous solution sample. Techniques of applying a turbidity correction have been described in literature and can be understood by those of ordinary skill in the art. A technique for correcting for turbidity includes determining a turbidity value for the turbid solution based on a Raman line intensity calibration data set for the solvent and determining a turbidity correction factor based on the turbidity value and a Raman line calibration data set for an analyte and applying the turbidity correction factor to the Raman line intensity of the analyte in the turbid solution and calculating a turbidity-corrected Raman line intensity for the analyte in the turbid solution. The turbidity-corrected Raman line intensity of the analyte in the turbid solution is then used to determine the concentration of the analyte in the turbid solution utilizing previously developed calibration data sets relating Raman line intensity to analyte concentration in solutions of negligible turbidity. Details of the technique are further described in U.S. patent application Ser. No. 14/597,614 on Jan. 15, 2015 by Joseph Victor Sinfield and Chukwukelue Kenneth Monwuba, and a technical paper titled "Assessment and Correction of Turbidity Effects on Raman Observations of Chemicals in Aqueous Solutions" by Joseph V. Sinfield and Chike K. Monwuba, APPLIED SPECTROSCOPY, Volume 68, Number 12, 2014, pages 1381-1392, both of which are incorporated herein by reference in their entirety.

Thus, the modified method begins with providing or obtaining a set of non-turbid aqueous chlorinated solvent calibration solutions which are solutions of water and a chlorinated solvent. In this set, each calibration solution has a chlorinated solvent concentration falling in a predetermined concentration range. The set should contain at least two calibration solutions with different chlorinated solvent concentrations falling within the predetermined concentration range. This predetermined concentration range can be based on prior information about the range concentrations expected in the solution sample. Then intensity of Raman return at a predetermined Raman shift associated with O—H stretching region of water for each of the plurality of non-turbid aqueous chlorinated solvent calibration solutions is measured. The predetermined Raman shift can be based on preliminary experiments in which Raman returns at different Raman shifts associated with O—H stretching region of water are measured, and specific Raman shift can be chosen based intensity, measurement sensitivity and error minimization. Thus, a calibration profile for non-turbid solutions is then developed relating chlorinated solvent concentrations of the plurality of the non-turbid aqueous chlorinated solvent calibration solutions in the set to the measured intensities of Raman return at the predetermined Raman shift associated with O—H stretching region of water for each of the non-turbid aqueous chlorinated solvent samples in the set of non-turbid aqueous chlorinated solvent calibration solutions. A turbid aqueous solution sample, whose chlorinated solvent concentration has to be determined, is then obtained. Then intensity of Raman return at the predetermined Raman shift associated with O—H stretching region of the turbid aqueous solution sample is measured. A turbidity correction is then applied to the measured of Raman return at the predetermined Raman shift associated with O—H stretching region of the turbid aqueous solution sample from the geographic region of interest to obtain a turbidity-corrected intensity. This turbidity-corrected intensity is compared to the calibration profile for non-turbid solutions described above. By this comparison, concentration of the chlorinated solvent in the turbid aqueous solution sample is determined.

Another method of determining concentration of a chlorinated solvent a turbid aqueous solution sample, whose chlorinated solvent concentration has to be determined, can also be described. This method begins with providing or obtaining a set of turbid aqueous chlorinated solvent calibration solutions which are solutions of water and a chlorinated solvent. Each sample in this set has a chlorinated solvent concentration falling in a predetermined concentration range. The set should contain at least two calibration solutions with different chlorinated solvent concentrations falling within the predetermined concentration range. This predetermined concentration range can be based on prior information about the range concentrations expected in the solution. Further, each calibration solution in this set has a turbidity value falling in a predetermined concentration range. This predetermined turbidity range can be based on prior information about the range of turbidity expected in the solution sample. Then intensity of Raman return at a predetermined Raman shift associated with O—H stretching region of water for each of the plurality of turbid aqueous chlorinated solvent calibration solutions in the set is measured. The predetermined Raman shift can be based on preliminary experiments in which Raman returns at different Raman shifts associated with O—H stretching region of water are measured, and specific Raman shift can be chosen based intensity, measurement sensitivity and error minimization. Thus, a calibration profile for turbid solutions is then developed relating chlorinated solvent concentrations of the plurality of the turbid aqueous chlorinated calibration solutions samples in the set to the measured intensities of Raman return at the predetermined Raman shift associated with O—H stretching region of water for each of the turbid aqueous chlorinated solvent calibration solutions in the set of non-turbid aqueous chlorinated solvent calibration solutions. A turbid aqueous solution sample whose chlorinated solvent concentration has to be determined is then obtained. Then, intensity of Raman return at the predetermined Raman shift associated with O—H stretching region of the turbid aqueous solution sample is measured. This measured intensity of Raman return at the predetermined Raman shift associated with O—H stretching region of the turbid aqueous solution sample is then compared to the calibration profile for turbid solutions described above. By this comparison, concentration of the chlorinated solvent in the turbid aqueous solution sample is determined.

Yet another method of determining concentration of a chlorinated solvent in a turbid aqueous solution sample, whose chlorinated solvent concentration has to be determined, can also be described. This method begins with providing or obtaining a set of turbid aqueous chlorinated solvent calibration solutions which are solutions of water and a chlorinated solvent. Each sample in this set has a chlorinated solvent concentration falling in a predetermined concentration range. The set should contain at least two calibration solutions with different chlorinated solvent concentrations falling within the predetermined concentration range. This predetermined concentration range can be based on prior information about the range concentrations expected in the solution. Further, each calibration solution in this set has a turbidity value falling in a predetermined concentration range. This predetermined turbidity range can be based on prior information about the range of turbidity expected in the solution sample. Then intensity of Raman return at a predetermined Raman shift associated with O—H stretching region of water for each of the plurality of turbid aqueous chlorinated solvent calibration solutions in the set is measured. The predetermined Raman shift can be based on preliminary experiments in which Raman returns at different Raman shifts associated with O—H stretching region of water are measured, and specific Raman shift can be chosen based intensity, measurement sensitivity and error minimization. A turbidity correction is then applied, following the techniques referred to above, to intensities of Raman return at a predetermined Raman shift associated with O—H stretching region of water for each of the plurality of turbid aqueous chlorinated solvent calibration solutions in the set. Then, a turbidity-corrected calibration profile for turbid solutions is then developed relating chlorinated solvent concentrations of the plurality of the turbid aqueous chlorinated calibration solutions samples in the set to the turbidity-corrected intensities of Raman return at the predetermined Raman shift associated with O—H stretching region of water for each of the turbid aqueous chlorinated solvent calibration solutions in the set of turbid aqueous chlorinated solvent calibration solutions. A turbid aqueous solution sample whose chlorinated solvent concentration has to be determined is then obtained. Then, intensity of Raman return at the predetermined Raman shift associated with O—H stretching region of the turbid aqueous solution sample is measured. A turbidity correction is then applied to intensity of Raman return at the predetermined Raman shift associated with O—H stretching region of the turbid aqueous solution sample. This turbidity-corrected intensity of Raman return at the predetermined Raman shift associated with O—H stretching region of the turbid aqueous solution sample is then compared to the turbidity-corrected calibration profile for turbid solutions described above. By this comparison, concentration of the chlorinated solvent in the turbid aqueous solution sample is determined.

In all the above methods, the predetermined concentration range for the chlorinated solvent calibration solutions can advantageously include a chlorinated solvent concentration of zero. In this context, zero concentration is understood to mean pure water as is generally understood in laboratories and in the definition of reagent grades and no chlorinated solvent is introduced.

In all the methods described in this disclosure, the aqueous solution sample (containing a chlorinated solvent), whose chlorinated solvent concentration has to be determined, can be from a geographic region of interest. This geographic region of interest can be a well, a body of water, a subsurface water environment, an aquifer, a waste water stream, and an industrial process stream, or like situations. Further, other possibilities exist for the source of the aqueous solution sample such as rain water, man-made samples and the like.

Aqueous media encountered in geographic regions of interest and/or in natural environment often contain suspended solids that can interfere with spectroscopic measurements. Removal of these solids, for example via filtration, can have adverse effects on the extent to which subsequent measurements are representative of actual field conditions under which the aqueous media are collected. In such cases, the methods described above for turbid aqueous solution sample have to be employed.

A chlorinated solvent of high interest is trichloroethylene or TCE. The methods described here are very much applicable to TCE. Thus the chlorinated solvent in all of the above methods can be TCE. Non-limiting examples of other solvents, whose concentrations can be measured using the method of this disclosure, are carbon tetrachloride and perchloroethylene.

While the above methods describe determining concentration of chlorinated solvents in turbid or non-turbid aqueous solutions, it must be recognized that these methods are applicable when more than one chlorinated solvent is present. That is the methods are applicable when the aqueous solution of interest contains an aggregate of chlorinated solvents. It should be noted that in a very complex environment that may involve more than one chlorinated solvent, one could perform a traditional chemical analysis test on a sample of water from the site to determine the constituents, and then use the methods described here to determine the presence and concentration of the aggregate chlorinated solvents. Thus in all the above methods, the chlorinated solvent can be an aggregate of two or more chlorinated solvents. The Raman spectra generated in the above methods can be used to identify individual chlorinated solvents present in the solution sample, while the methods described above can be used to quantify the identified chlorinated solvents. The methods described here would quantify the aggregate chlorinated solvent with our method. Water and the OH range contain several Raman vibrations and some are more susceptible to some chlorinated solvents than others so there is the possibility that one could identify the chlorinated solvents with some detailed studies. In such case, one might use more than one water Raman line in the OH-region to facilitate multi-chlorinated solvent analysis.

Thus this disclosure describes techniques to detect as well as quantify chlorinated solvents in an aqueous solution containing chlorinated solvent or chlorinated solvents.

It is possible to use other regions of the water Raman return for this purpose. It is seen that the O—H stretching region gave the strongest Raman response for the instrument employed in the studies of this disclosure. Methods based on O—H stretching region are considered to be a more accurate representation of the response of water and provide greatest sensitivity. It should be noted that in a very complex environment that may involve more than one chlorinated solvent, one could perform a traditional chemical analysis test on a sample of water from the site to determine the constituents, and then use the Raman analysis to infer the presence of the aggregate chlorinated solvent.

It should be noted that the methods described in this disclosure for determining chlorinated solvent concentrations can be adapted for analysis of aqueous systems containing other Group 7 elements of the periodic table such as fluorine, bromine, or iodine for determining and monitoring fluorine, bromine and iodine respectively.

While many solvents exist in many field situations, the methods described here can be used when the solvent for the chlorinated compounds is water. Water tends to be a primary solvent in many different environmental contexts and industrial operations, and Raman signatures of water tend to be shifted from the Raman signatures of many chemicals of interest.

As mentioned above, the relationship between chlorinated solvent concentration and the measured Raman intensity of O—H region of water in a chlorinated solvent solution is inverse. That is, as chlorinated solvent concentration increases, the measured Raman intensity of the O—H region of water in the chlorinated solvent solution decreases. It should be further recognized that this inverse relationship has an advantageous consequence of increased sensitivity when the chlorinated solvent concentration is low, giving a desirable high signal to noise ratio in measurements at low concentrations of the chlorinated solvent.

It is to be further recognized that methods described in this disclosure for determining chlorinated solvent concentrations in turbid or non-turbid aqueous solutions of interest applicable in practical monitoring scenarios in the field without the need for "pass through" optical observations, and do not need for a priori modeling thus enabling corrections in "real time" for concentration determinations and thereby accounting for in-situ changes. These methods also eliminate the need to deeply penetrate the sample with radiation or analyze large areas, and hence these methods enable concentration measurements in "real time" to account for in-situ changes, and also enable targeted, single-sided optical observations.

In various embodiments of the present invention there is no requirement to obtain a test sample of the solution being tested. Instead, various embodiments contemplate the notion of an "in-situ" measurement. In such cases, the technician will put the measuring equipment right into the natural setting (e.g., in a well, in a stream, or underground in a soil probe like a cone penetrometer). Thus we are not obtaining a sample, but instead just measuring an unaltered/unprepared environment that is in its natural state. However, one can also obtain a sample of the turbid or non-turbid solution of interest from the field. Thus the turbid solutions that are analyzed for the concentration of an analyte can be from a well, a body of water, a subsurface water environment, an aquifer, a waste water stream, and an industrial process stream. These are to be recognized as non-limiting examples for the source of the turbid solution. The methods described above will also work for samples obtained from the field. Care should be taken that samples so obtained from the field are representative of the field conditions, especially in terms of turbidity and concentration of the chlorinated solvents of interest.

It should be noted that the turbidity values that can use the methods described here have very wide range. It is expected that the methods described in this disclosure can be used for turbid solutions with turbidly values ranging from 3-300 NTUs. A higher value for the range is possible.

It should be further recognized that the methods described here are convenient for "in-situ" measurements. Further, the methods described are especially suitable where the chlorinated solvent concentration is low and turbidity values for the solutions are high (40-200 NTUs as a non-limiting range). The methods described here can be used for chlorinated solvent concentrations as low as a few parts per million.

The measurement techniques described in this disclosure can be used to detect the presence of one or more of chlorinated compounds by comparing the Raman intensity of the O—H stretching region at a predetermined Raman shift to that of water with no presence of chlorinated solvents. While such comparison of spectra leads to detecting the presence of the chlorinated compounds, quantification would require the methods described in this disclosure. Simple comparison techniques such as this for detection purposes can lead to inexpensive sensors for monitoring water quality.

While the present disclosure has been described with reference to certain embodiments, it will be apparent to those of ordinary skill in the art that other embodiments and implementations are possible that are within the scope of the present disclosure without departing from the spirit and scope of the present disclosure. Thus, the implementations should not be limited to the particular limitations described. Other implementations may be possible. It is therefore intended that the foregoing detailed description be regarded as illustrative rather than limiting. Thus, this disclosure is limited only by the following claims.

The invention claimed is:

1. A method comprising:
   providing a plurality of non-turbid aqueous chlorinated solvent calibration solutions, the calibration solutions comprising solutions of water and a chlorinated solvent, each calibration solution having a concentration of the chlorinated solvent within a predetermined concentration range, at least two of the chlorinated solvent calibration solutions having different concentrations of the chlorinated solvent within the predetermined concentration range;
measuring intensity of Raman return at a predetermined Raman shift associated with O—H stretching region of water for each of the plurality of non-turbid aqueous chlorinated solvent calibration solutions;
developing a calibration profile for non-turbid solutions relating chlorinated solvent concentrations of the plurality of the non-turbid aqueous chlorinated solvent calibration solutions to the measured intensities;
obtaining a non-turbid aqueous solution sample whose chlorinated solvent concentration has to be determined, the sample containing the chlorinated solvent;
measuring intensity of Raman return at the predetermined Raman shift associated with O—H stretching region of the non-turbid aqueous solution sample;
comparing the intensity of Raman return at the predetermined Raman shift associated with O—H stretching region of the non-turbid aqueous solution sample to the calibration profile for non-turbid solutions; and
determining the concentration of the chlorinated solvent in the non-turbid aqueous solution sample.

2. The method of claim 1, wherein the predetermined concentration range includes zero concentration.

3. The method of claim 1, wherein the non-turbid aqueous solution sample whose chlorinated solvent concentration has to be determined is taken from a geographic region of interest.

4. The method of claim 3, wherein the geographic region of interest is a well, a body of water, a subsurface water environment, an aquifer, a waste water stream, or an industrial process stream.

5. The method of claim 3, wherein the chlorinated solvent is trichloroethylene.

6. The method of claim 3, wherein the chlorinated solvent is an aggregate of chlorinated solvents.

7. The method of claim 1, wherein the chlorinated solvent is trichloroethylene.

8. The method of claim 1, wherein the chlorinated solvent is an aggregate of chlorinated solvents.

9. A method comprising:
providing a plurality of non-turbid aqueous chlorinated solvent calibration solutions, the calibration solutions comprising solutions of water and a chlorinated solvent, each calibration solution having a concentration of the chlorinated solvent within a predetermined concentration range, at least two of the chlorinated solvent calibration solutions having different concentrations of the chlorinated solvent within the predetermined concentration range;
measuring intensity of Raman return at a predetermined Raman shift associated with O—H stretching region of water for each of the plurality of non-turbid aqueous chlorinated solvent calibration solutions;
developing a calibration profile for non-turbid solutions relating concentrations of the plurality of the non-turbid aqueous chlorinated solvent calibration solutions to the measured intensities;
obtaining a turbid aqueous solution sample whose chlorinated solvent concentration has to be determined, the sample containing the chlorinated solvent;
measuring intensity of Raman return at the predetermined Raman shift associated with O—H stretching region of the turbid aqueous solution sample;
applying a turbidity correction to the measured of Raman return at the predetermined Raman shift associated with O—H stretching region of the turbid aqueous solution sample to obtain a turbidity-corrected intensity; and
comparing the turbidity-corrected intensity to the calibration profile for non-turbid solutions; and
determining concentration of the chlorinated solvent in the turbid aqueous solution sample.

10. The method of claim 9, wherein the predetermined concentration range includes zero concentration.

11. The method of claim 9, wherein the turbid aqueous solution sample whose chlorinated solvent concentration has to be determined is taken from a geographic region of interest.

12. The method of claim 11, wherein the geographic region of interest is a well, a body of water, a subsurface water environment, an aquifer, a waste water stream, or an industrial process stream.

13. The method of claim 11, wherein the chlorinated solvent is trichloroethylene.

14. The method of claim 11, wherein the chlorinated solvent is an aggregate of chlorinated solvents.

15. The method of claim 9, wherein the chlorinated solvent is trichloroethylene.

16. The method of claim 9, wherein the chlorinated solvent is an aggregate of chlorinated solvents.

17. A method comprising:
providing a plurality of turbid aqueous chlorinated solvent calibration solutions, the calibrations solutions comprising solutions of water and a chlorinated solvent, each calibration solution having a turbidity value in a predetermined turbidity range, each calibration solution having a concentration of the chlorinated solvent within a predetermined concentration range, at least two of the chlorinated solvent calibration solutions samples having different concentrations within the predetermined range;
measuring intensity of Raman return at a predetermined Raman shift associated with O—H stretching region of water for each of the plurality of turbid aqueous chlorinated solvent calibration solutions;
developing a calibration profile for turbid solutions relating concentrations of the plurality of the turbid aqueous chlorinated solvent samples to the measured intensities;
obtaining a turbid aqueous solution sample whose chlorinated solvent concentration has to be determined, the sample containing the chlorinated solvent;
measuring intensity of Raman return at the predetermined Raman shift associated with O—H stretching region of the turbid aqueous solution sample;
comparing the intensity of Raman return at the predetermined Raman shift associated with O—H stretching region of the turbid aqueous solution sample to the calibration profile for turbid solutions; and
determining concentration of the chlorinated solvent in the turbid aqueous solution sample.

18. The method of claim 17, wherein the predetermined concentration range includes zero concentration.

19. The method of claim 17, wherein the turbid aqueous solution sample whose chlorinated solvent concentration has to be determined is taken from a geographic region of interest.

20. The method of claim 19, wherein the geographic region of interest is a well, a body of water, a subsurface water environment, an aquifer, a waste water stream, or an industrial process stream.

* * * * *